US012016895B2

(12) United States Patent
Carle

(10) Patent No.: US 12,016,895 B2
(45) Date of Patent: *Jun. 25, 2024

(54) SKIN CARE FORMULATION

(71) Applicant: MARY KAY INC., Addison, TX (US)

(72) Inventor: Tiffany Carle, Dallas, TX (US)

(73) Assignee: MARY KAY INC., Addison, TX (US)

(*) Notice: Subject to any disclaimer, the term of this patent is extended or adjusted under 35 U.S.C. 154(b) by 175 days.

This patent is subject to a terminal disclaimer.

(21) Appl. No.: 16/838,338

(22) Filed: Apr. 2, 2020

(65) Prior Publication Data

US 2020/0230195 A1 Jul. 23, 2020

Related U.S. Application Data

(63) Continuation of application No. 15/355,297, filed on Nov. 18, 2016, now Pat. No. 10,639,344, which is a continuation of application No. 13/710,097, filed on Dec. 10, 2012, now Pat. No. 9,526,689.

(60) Provisional application No. 61/570,719, filed on Dec. 14, 2011, provisional application No. 61/569,034, filed on Dec. 9, 2011.

(51) Int. Cl.
A61K 36/87 (2006.01)
A61K 8/49 (2006.01)
A61K 8/97 (2017.01)
A61K 8/9789 (2017.01)
A61K 9/00 (2006.01)
A61K 9/107 (2006.01)
A61K 31/05 (2006.01)
A61K 31/353 (2006.01)
A61K 31/56 (2006.01)
A61K 31/704 (2006.01)
A61K 36/23 (2006.01)
A61K 36/575 (2006.01)
A61K 36/82 (2006.01)
A61Q 19/00 (2006.01)
A61Q 19/08 (2006.01)

(52) U.S. Cl.
CPC ............ A61K 36/87 (2013.01); A61K 8/498 (2013.01); A61K 8/97 (2013.01); A61K 8/9789 (2017.08); A61K 9/0014 (2013.01); A61K 9/107 (2013.01); A61K 31/05 (2013.01); A61K 31/353 (2013.01); A61K 31/56 (2013.01); A61K 31/704 (2013.01); A61K 36/23 (2013.01); A61K 36/575 (2013.01); A61K 36/82 (2013.01); A61Q 19/00 (2013.01); A61Q 19/08 (2013.01); A61K 2236/30 (2013.01)

(58) Field of Classification Search
CPC .................................................. A61K 36/87
See application file for complete search history.

(56) References Cited

U.S. PATENT DOCUMENTS

| 6,096,359 | A | 8/2000 | Bombardelli et al. |
| 6,210,680 | B1 | 4/2001 | Jia et al. |
| 6,884,783 | B2 | 4/2005 | Jia et al. |
| 7,160,560 | B2 | 1/2007 | Pinnell |
| 7,214,395 | B2 | 5/2007 | DiPierro |
| 7,354,610 | B2 | 4/2008 | DiPierro |
| 7,744,932 | B2 * | 6/2010 | Faller ................ A61K 36/752 424/725 |
| 2004/0146539 | A1 | 7/2004 | Gupta |
| 2004/0161435 | A1 | 8/2004 | Gupta |
| 2004/0208902 | A1 | 10/2004 | Gupta |
| 2004/0219124 | A1 | 11/2004 | Gupta |
| 2005/0043398 | A1 | 2/2005 | Carola et al. |
| 2008/0260869 | A1 | 10/2008 | Faller et al. |
| 2009/0117061 | A1 | 5/2009 | Gross |
| 2010/0247693 | A1 | 9/2010 | Marini |
| 2011/0229536 | A1 | 9/2011 | Kvitnitsky et al. |

FOREIGN PATENT DOCUMENTS

| WO | WO 2008/132149 | 11/2008 | |
| WO | WO-2008132149 A1 * | 11/2008 | ............. A61P 31/00 |
| WO | WO 2010/037545 | 4/2010 | |
| WO | WO 2011/103449 | 8/2011 | |
| WO | WO 2012/154949 | 11/2012 | |

OTHER PUBLICATIONS

Stargrove et al. "Gotu Kola" from "Herb, Nutrient and Drug Interactions". pp. 88-90. (Year: 2008).*
Han et. al. retrieved on Dec. 20, 2023 (Effects of green tea polyphenol on preservation of human saphenous vein, Journal of Biotech., 110 (2004) 109-117) (Year: 2004).*
Carola et al., "Dihydroxy Methylchromone: A Nature-Like Anti-Aging Ingredient", *SOFW-Journal*, 136(4):2-10, 2010.
International Cosmetic Ingredient Dictionary and Handbook 12th Ed., vol. 1, pp. 458-459, 2008.
International Cosmetic Ingredient Dictionary and Handbook 12th Ed., vol. 3, pp. 2892, 2008.
International Cosmetic Ingredient Dictionary and Handbook 12th Ed., vol. 3, pp. 2713, 2008.
International Search Report and Written Opinion issued in PCT Application No. PCT/US2012/068796, mailed Apr. 1, 2013.

(Continued)

Primary Examiner — Aaron J Kosar
Assistant Examiner — Jacob A Boeckelman
(74) Attorney, Agent, or Firm — NORTON ROSE FULBRIGHT US LLP

(57) ABSTRACT

A method of treating telangiectasia in a subject in need thereof is disclosed. The method includes topically applying to skin of said subject in need of treatment of telangiectasia a composition comprising effective amounts of an extract of *Centella asiatica* leaf and an extract of *Vitis vinifera* seed to disrupt endothelial tubes in skin.

12 Claims, No Drawings

(56) References Cited

OTHER PUBLICATIONS

Stargrove et al. "Gotu Kola" from "Herb, Nutrient and Drug Interactions" pp. 88-90, 2008.
Supplemental European Search Report issued May 19, 2015 in European Application No. 12856021.6.

\* cited by examiner

SKIN CARE FORMULATION

CROSS REFERENCE TO RELATED APPLICATIONS

This application is a continuation of U.S. patent application Ser. No. 15/355,297, filed Nov. 18, 2016, which is a continuation of U.S. patent application Ser. No. 13/710,097, filed Dec. 10, 2012 (now issued as U.S. Pat. No. 9,526,689), which claims the benefit of U.S. Provisional Application No. 61/570,719, filed Dec. 14, 2011, and U.S. Provisional Application No. 61/569,034, filed Dec. 9, 2011. The contents of the referenced applications are incorporated into the present application by reference.

BACKGROUND OF THE INVENTION

A. Field of the Invention

The present invention relates generally to skin care compositions. In one particular aspect, the composition includes a combination of *Centella asiatica* extract, *Vitis vinifera* seed extract, *Magnolia* bark extract, *Camellia sinensis* extract, and dihydroxymethylchromone. The inventor discovered that such a combination works especially well in treating telangiectasia or spider veins.

B. Description of Related Art

Telangiectasia can be characterized in a general sense as a dilatation of small blood vessels such as veins that are located near the surface of a person's skin. Such dilation can be visible on the skin in the form of red, blue, purple or blotchy skin. In some instances, the dilated blood vessels present on the skin in a tree branch-like, or a matting or linear pattern, or spider-web-like appearance, which is commonly referred to as "spider veins." Spider veins, which usually appear on the thighs, lower legs, and face of people, are visually unappealing.

Current methods of treating spider veins include sclerotherapy, surgery, radiofrequency, and laser ablation. Such treatment methods can cause damage to skin, and oftentimes require professional assistance.

SUMMARY OF THE INVENTION

The inventor has discovered that a combination of ingredients can be used in a topical skin formulation to treat telangiectasia or spider veins. In addition to treating the afflicted skin, the composition can also be beneficial to the skin by, for example, moisturizing the skin. Therefore, the composition does not damage skin as with other treatment methods. Further, the composition can be applied by the user without the assistance of a professional.

In one instance, there is disclosed a composition, and a method of treating telangiectasia comprising topically applying to skin in need of treatment said composition. The composition can include a combination of extracts and/or ingredients from *Centella asiatica, Vitis vinifera* seed, *Magnolia* bark, *Camellia sinensis* and/or dihydroxymethylchromone, or any combination thereof of (e.g., at least 2, 3, or 4 of said extracts), all of said extracts or ingredients, or specific combinations (e.g., extracts from *Centella asiatica* and *Vitis vinifera* seed; extracts from *Centella asiatica* and *Magnolia* bark; extracts from *Centella asiatica* and *Camellia sinensis*; extract from *Centella asiatica* and dihydroxymethylchromone; extracts from *Vitis vinifera* seed and *Magnolia* bark; extracts from *Vitis vinifera* seed and *Camellia sinensis*; extract from *Vitis vinifera* seed and dihydroxymethylchromone; extracts from *Magnolia* bark and *Camellia sinensis*; extract from *Magnolia* bark and dihydroxymethylchromone; extract from *Camellia sinensis* and dihydroxymethylchromone; etc.). In one instance, the *Magnolia* bark extract is *Magnolia grandiflora* bark extract that includes honokiol and magnolol, the *Centella asiatica* extract includes asiaticoside, madecassic acid, and asiatic acid, the *Camellia sinensis* extract is *Camellia sinensis* leaf extract that includes epigallocatechin gallate, and the *Vitis vinifera* seed extract includes polyphenols.

"A combination of extracts" can include individual extracts that are individually included into a composition or can include two or more extracts that are first combined and then added to a composition. In particular embodiments, the composition includes all five of said extracts and ingredients. The inventors discovered that *Centella asiatica* extract and *Vitis vinifera* seed extract can be used to promote endothelial tube disruption, which can limit and destroy the formation of spider veins. Dihydroxymethylchromone has been found to thicken the epidermis, which can work to reduce the appearance of spider veins. *Magnolia* bark extract has been found to inhibit angiogenesis, which can limit vein growth. *Camellia sinensis* can act as a vasoconstrictor, which can push the blood out of the veins, thereby making the spider veins less apparent on the surface of the skin. The *Camellia sinensis* extract can include a polyphenol compound such as epigallocatechin gallate. The inventors further discovered that when each of these ingredients are combined, they have a synergistic effect in limiting the formation of spider veins while also reducing the appearance of existing veins. Thus, the combination works extremely well in treating telangiectasia such as spider veins. In certain aspects, the composition is applied to the skin and remains on the skin for at least 5, 10, 15, 30, or more minutes, or 1, 4, 8, 12, 16, 20, or 24 hours after topical application. The composition can be applied to telangiectasia (e.g., spider veins) that is present on facial skin, leg skin, ankle skin, arm skin, etc. In certain aspects, the composition can be formulated as a cream, gel, or lotion. In some instances, the composition is an emulsion (e.g., oil-in-water, water-in-oil, hydrophilic-in-hydrophobic, hydrophobic-in-hydrophilic, silicone-in-water, water-in-silicone, etc.). The composition can further include a moisturization agent, a UV absorbing agent, anti-oxidant, structuring agent, emulsifier, silicone containing compound, essential oil, thickening agent, and/or a preservative, such as those disclosed throughout this specification. The composition can include a pharmaceutical ingredient, such as those disclosed throughout this specification. In some instances, the composition can further include *Tambourissa trichophylla* leaf extract. The composition can include 0.0001 to 10% by weight (or 0.001, 0.01, 0.1, 1, 2, 3, 4, 5, 6, 7, 8, 9, or 10% by weight or more) of an extract from *Centella asiatica*, 0.0001 to 10% by weight of an extract from *Vitis vinifera* seed (or 0.001, 0.01, 0.1, 1, 2, 3, 4, 5, 6, 7, 8, 9, or 10% by weight or more), 0.0001 to 10% by weight of an extract from *Magnolia* bark (or 0.001, 0.01, 0.1, 1, 2, 3, 4, 5, 6, 7, 8, 9, or 10% by weight or more), 0.0001 to 10% by weight of an extract from *Camellia sinensis* (or 0.001, 0.01, 0.1, 1, 2, 3, 4, 5, 6, 7, 8, 9, or 10% by weight or more), and/or 0.0001 to 10% by weight of dihydroxymethylchromone (or 0.001, 0.01, 0.1, 1, 2, 3, 4, 5, 6, 7, 8, 9, or 10% by weight or more). In certain aspects, the composition can include 0.0001 to 10% by weight of an extract from *Tambourissa trichophylla* leaf (or 0.001, 0.01, 0.1, 1, 2, 3, 4, 5, 6, 7, 8, 9, or 10% by weight or more). The

*Magnolia* bark extract can be *Magnolia grandiflora* bark extract, *Magnolia officinalis* bark extract, or *Magnolia obovata* bark extract. In certain aspects, the extract is from *Magnolia grandiflora* bark. The *Centella asiatica* extract can be a culture from *Centella asiatica* meristem. The *Camellia sinensis* extract can be *Camellia sinensis* leaf extract and/or can include a polyphenol compound such as epigallocatechin gallate. The *Centella asiatica* extract, *Vitis vinifera* seed extract, *Magnolia* bark extract, and/or *Camellia sinensis* extract can be an aqueous, alcoholic, hydro-alcoholic, or oil-based extract. In particular embodiments, the extracts are an alcoholic extract or a combination of water/alcohol extract.

Also disclosed is a composition, and a method of using the composition to treat skin comprising topically applying to skin in need of treatment said composition. The composition can include at least one, two, three, four, or all of a *Centella asiatica* extract, a *Vitis vinifera* seed extract, a *Magnolia* bark extract, a *Camellia sinensis* extract, and/or dihydroxymethylchromone. In some instances, the composition can be applied to telangiectasiatic skin, skin that presents spider veins, and/or skin that presents varicose veins. In certain aspects, the composition can be used to constrict the flow of blood in veins and small blood vessels such as arterioles, a capillaries, and/or a venules. The composition could further includes *Tambourissa trichophylla* leaf extract. In one instance the combination of ingredients can be *Centella asiatica* extract and *Vitis vinifera* seed extract. In one instance, the combination can be *Centella asiatica* extract and *Magnolia* bark extract. In one instance, the combination can be *Centella asiatica* extract and *Camellia sinensis* extract. In one instance, the combination can be *Centella asiatica* extract and dihydroxymethylchromone. In one instance, the combination can be *Vitis vinifera* seed extract and *Magnolia* bark extract. In one instance, the combination can be *Vitis vinifera* seed extract and *Camellia sinensis* extract. In one instance, the combination can be *Centella Vitis vinifera* seed extract and dihydroxymethylchromone. In one instance, the combination can be *Magnolia* bark extract and *Camellia sinensis* extract. In one instance, the combination can be *Magnolia* bark extract and dihydroxymethylchromone. In one instance the combination can be *Camellia sinensis* extract and dihydroxymethylchromone. Other aspects of the composition can be similar to that as described in the paragraph directly above this paragraph, which is incorporated by reference (e.g., amount of ingredients, additional ingredients, formulation of composition, specific extracts, etc.). In one instance, the *Magnolia* bark extract is *Magnolia grandiflora* bark extract that includes honokiol and magnolol, the *Centella asiatica* extract includes asiaticoside, madecassic acid, and asiatic acid, the *Camellia sinensis* extract is *Camellia sinensis* leaf extract that includes epigallocatechin gallate, and the *Vitis vinifera* seed extract includes polyphenols.

The compositions of the present invention can be formulated into topical skin care compositions. The compositions can be cosmetic compositions. In other aspects, the compositions can be included in a cosmetic vehicle. Non-limiting examples of cosmetic vehicles are disclosed in other sections of this specification and are known to those of skill in the art. Examples of cosmetic vehicles include emulsions (e.g., oil-in-water and water-in-oil emulsions), creams, lotions, solutions (e.g., aqueous or hydro-alcoholic solutions), anhydrous bases (e.g., lipstick or a powder), gels, and ointments. In other non-limiting embodiments, the compositions of the present invention can be included in anti-aging, cleansing, or moisturizing products. The compositions can also be formulated for topical skin application at least 1, 2, 3, 4, 5, 6, 7, or more times a day during use. In other aspects of the present invention, compositions can be storage stable or color stable, or both. It is also contemplated that the viscosity of the composition can be selected to achieve a desired result (e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000 cps, etc., as measured on a Brookfield Viscometer using a TC spindle at 2.5 rpm at 25° C.). The compositions in non-limiting aspects can have a pH of about 6 to about 9. In other aspects, the pH can be 1, 2, 3, 4, 5, 6, 7, 8, 9, 10, 11, 12, 13, or 14. Compositions of the present invention can have UVA and UVB absorption properties. The compositions can have an sun protection factor (SPF) of 2, 3, 4, 5, 6, 7, 8, 9, 10, 11, 12, 13, 14, 15, 20, 25, 30, 35, 40, 45, 50, 55, 60, or more, or any integer or derivative therein. The compositions can be sunscreen lotions, sprays, or creams. In particular aspects, the compositions can be oil-free, substantially anhydrous, and/or anhydrous. Other aspects include compositions having water.

The compositions of the present invention can also include any one of, any combination of, or all of the following additional ingredients: water, a chelating agent, a moisturizing agent, a preservative, a thickening agent, a silicone containing compound, an essential oil, a structuring agent, a vitamin, a pharmaceutical ingredient, or an antioxidant, or any combination of such ingredients or mixtures of such ingredients. In certain aspects, the composition can include at least two, three, four, five, six, seven, eight, nine, ten, or all of these additional ingredients identified in the previous sentence. Non-limiting examples of these additional ingredients are identified throughout this specification and are incorporated into this section by reference. The amounts of such ingredients can range from 0.0001% to 99.9% by weight or volume of the composition, or any integer or range in between as disclosed in other sections of this specification, which are incorporated into this paragraph by reference.

The compositions can also be used to treat or prevent a variety of skin conditions other than telangiectasia. For instance, the compositions can be used to treat or prevent a fine line or wrinkle, dry or flaky skin, erythema, sensitive skin, or inflamed skin. In particular aspects, erythema, sensitive skin, or inflamed skin is caused by skin sunburn, electrical treatments of skin, skin burns, contact allergies, systemic allergies, skin toxicity, exercise, insect stings, bacterial infection, viral infection, fungal infection, protozoa infection, massage, or windburn. In other aspects, the following additional skin conditions can be treated or prevented in accordance with the methods and compositions disclosed throughout the specification and claims: pruritus, lentigo, age spots, senile purpura, keratosis, melasma, blotches, nodules, sun damaged skin, dermatitis (including, but not limited to seborrheic dermatitis, nummular dermatitis, contact dermatitis, atopic dermatitis, exfoliative dermatitis, perioral dermatitis, and stasis dermatitis), psoriasis, folliculitis, rosacea, acne, impetigo, erysipelas, erythrasma, eczema, and other inflammatory skin conditions. In certain non-limiting aspects, the skin condition can be caused by exposure to UV light, age, irradiation, chronic sun exposure, environmental pollutants, air pollution, wind, cold, heat, chemicals, disease pathologies, smoking, or lack of nutrition. The skin can be facial skin or non-facial skin (e.g., arms, legs, hands, chest, back, feet, etc.). The method can further comprise identifying a person in need of skin treatment. The person can be a male or female. The age of the person can be at least 1, 2, 3, 4, 5, 6, 7, 8, 9, 10, 15, 20, 25, 30, 35, 40, 45, 50, 55, 60, 65, 70, 75, 80, 85, 90, 95, or more years old, or any range derivable therein. The method can also include topically applying an amount effective to: increase the stratum corneum turnover rate of the skin; increase collagen synthesis in fibroblasts; increase cellular anti-oxidant defense mechanisms (e.g., exogenous additions of anti-oxidants can bolster, replenish, or prevent the loss of cellular antioxidants such as catalase and glutathione in skin cells (e.g., keratinocytes, melanocytes, langerhans cells, etc.) which will reduce or prevent oxidative damage to the skin, cellular, proteins, and lipids); inhibit melanin production in melanocytes; reduce or prevent oxidative damage to skin (including reducing the amount lipid peroxides and/or protein oxidation in the skin).

Also disclosed is a method of reducing the appearance of uneven skin tone comprising topically applying any one of the compositions disclosed throughout the specification and claims to skin having an uneven skin tone, wherein topical application of the composition to uneven skin tone reduces the appearance of uneven skin tone. In one instance, the composition includes dihydroxymethylchromone *Centella asiatica* extract, *Vitis vinifera* seed extract, *Magnolia* bark extract, and/or *Camellia sinensis* extract.

In another embodiment, there is disclosed a method of reducing pain associated with erythema, sensitive skin, or inflamed skin, comprising topically applying any one of the compositions disclosed throughout the specification and claims to erythemic, sensitive, or inflamed skin, wherein topical application of the composition to erythemic, sensitive, or inflamed skin reduces the pain associated with erythema, sensitive skin, or inflamed skin. In one instance, the composition includes dihydroxymethylchromone *Centella asiatica* extract, *Vitis vinifera* seed extract, *Magnolia* bark extract, and/or *Camellia sinensis* extract.

In still another aspect, there is disclosed a method of reducing the appearance of symptoms associated with erythema, sensitive skin, or inflamed skin, comprising topically applying any one of the compositions disclosed throughout the specification and claims erythemic, sensitive, or inflamed skin, wherein topical application of the composition to erythemic, sensitive, or inflamed skin reduces the appearance of symptoms associated with erythema, sensitive skin, or inflamed skin. In one instance, the composition includes dihydroxymethylchromone *Centella asiatica* extract, *Vitis vinifera* seed extract, *Magnolia* bark extract, and/or *Camellia sinensis* extract.

In other aspect, there is disclosed a method of increasing collagen production in a skin cell comprising topically applying any one of the compositions disclosed throughout the specification and claims to a skin cell in need of collagen production, wherein the topical application of the composition to the skin cell increases collagen production in the skin cell. Non-limiting examples of such cells include human epidermal keratinocyte, human fibroblast dermal cell, human melanocytes, three dimensional human cell-derived in vitro tissue equivalents comprising human keratinocytes, human fibroblasts, or human melanocytes, or any combination thereof (e.g., combination of human keratinocytes and human fibroblasts or a combination of human keratinocytes and human melanocytes). In one instance, the composition includes dihydroxymethylchromone *Centella asiatica* extract, *Vitis vinifera* seed extract, *Magnolia* bark extract, and/or *Camellia sinensis* extract.

Also disclosed is a method of lightening skin or evening skin tone comprising applying any one of the compositions disclosed throughout the specification and claims to skin. The method can further comprise identify a person in need of lightening skin or evening skin tone. The methods can further include inhibiting melanogenesis in a skin cell, inhibiting tyrosinase or tyrosinase synthesis in a skin cell, or inhibiting melanin transport to keratinocytes in a skin cell. The composition can act as an alpha melanin stimulatory hormone antagonist. The composition can even out pigmentation of the skin. In non-limiting aspect, lightening skin can include reducing the appearance of an age spot, a skin discoloration, or a freckle by topical application of the composition to skin having an age spot, skin discoloration, a freckle, etc. In one instance, the composition includes dihydroxymethylchromone *Centella asiatica* extract, *Vitis vinifera* seed extract, *Magnolia* bark extract, and/or *Camellia sinensis* extract.

Also disclosed is a method of treating hyperpigmentation comprising applying any one of the compositions disclosed throughout the specification and claims to skin. The method can also comprise identifying a person in need of treating hyperpigmentation. Additional methods contemplated by the inventor include methods for reducing the appearance of an age spot, a skin discoloration, or a freckle, reducing or preventing the appearance of fine lines or wrinkles in skin, or increasing the firmness of skin. In one instance, the composition includes dihydroxymethylchromone *Centella asiatica* extract, *Vitis vinifera* seed extract, *Magnolia* bark extract, and/or *Camellia sinensis* extract.

Also contemplated are kits that include any one of the compositions disclosed throughout the specification and claims. In certain embodiments, the composition is comprised in a container. The container can be a bottle, dispenser, or package. The container can dispense a pre-determined amount of the composition. In certain aspects, the compositions is dispensed in a spray, dollop, or liquid. The container can include indicia on its surface. The indicia can be a word, an abbreviation, a picture, or a symbol.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a foundation, a night cream, a lipstick, a cleanser, a toner, a sunscreen, a mask, or an anti-aging product.

The compositions and methods for their use can "comprise," "consist essentially of," or "consist of" any of the ingredients disclosed throughout the specification. For purposes of consisting essentially of means that inclusion of additional ingredients in the compositions do not materially affect the beneficial properties of the compositions for treating telangiectasia or spider veins. For instance, if a composition "consists essentially of" any one of, any combination of, or 2, 3, 4, or all 5 of dihydroxymethylchromone, *Centella asiatica* extract, *Vitis vinifera* seed extract, *Magnolia* bark extract, and *Camellia sinensis* extract, said composition excludes any ingredients that would materially affect the beneficial properties of the compositions for treating telangiectasia or spider veins. For instance, ingredients that can act as a vasodilator could exasperate the appearance of telangiectasia or spider veins rather than treating said condition.

It is contemplated that any embodiment discussed in this specification can be implemented with respect to any method or composition of the invention, and vice versa. Furthermore, compositions of the invention can be used to achieve methods of the invention.

In one embodiment, compositions of the present invention can be pharmaceutically or cosmetically elegant. "Pharmaceutically elegant" and/or "cosmetically elegant" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

"Topical application" means to apply or spread a composition onto the surface of keratinous tissue. "Topical skin composition" includes compositions suitable for topical application on keratinous tissue. Such compositions are typically dermatologically-acceptable in that they do not have undue toxicity, incompatibility, instability, allergic response, and the like, when applied to skin. Topical skin care compositions of the present invention can have a selected viscosity to avoid significant dripping or pooling after application to skin.

"Keratinous tissue" includes keratin-containing layers disposed as the outermost protective covering of mammals and includes, but is not limited to, skin, hair and nails.

A "non-volatile oil" includes those substance that will not evaporate at ordinary or room temperature.

The terms "mixture," "mix," and "mixing" or any variants of these terms, when used in the claims and/or specification includes, stirring, blending, dispersing, milling, homogenizing, and other similar methods. The mixing of the components or ingredients of the disclosed compositions can form into a solution. In other embodiments, the mixtures may not form a solution. The ingredients/components can also exist as undissolved colloidal suspensions.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting," "reducing," "treating," or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

Telangiectasiasic skin is visually unappealing. It can result in dilated blood vessels (e.g., veins) near the surface of skin, which presents as red, purple, and/or blue lines on skin, oftentimes referred to as "spider veins." The lines can measure less than 1-3 mm in width and several millimeters to centimeters in length. Telangiectasias is common in healthy people, and can be caused by overexposure to sun or aging. It oftentimes afflicts the nose, cheeks, and chin on a person's face or the thighs, below the knees, and on the ankles, all of which are highly visible areas of the human body.

Instead of using the traditional procedures such as sclerotherapy, surgery, radiofrequency, and laser ablation, the inventor discovered a combination of ingredients that, when combined, work to reduce the appearance of Telangiectasias such as spider veins while also providing additional benefits to skin. These and other non-limiting aspects of the present invention are described in the following subsections.

A. Active Ingredients

As explained above, topical skin care compositions of the present invention can include *Centella asiatica* extract, *Vitis vinifera* seed extract, *Magnolia* bark extract, *Camellia sinensis* extract, and/or dihydroxymethylchromone. In certain aspects, *Tambourissa trichophylla* leaf extract can also be included in the combination. With respect to *Centella asiatica* extract, the *Centella asiatica* plant is a small herbaceous plant that is native to countries such as India, Sri Lanka, Australia, Indonesia, Malaysia, Melanesia, Papua New Guinea, and other parts of Asia. Extracts from this plant are commercially available from a wide range of sources (see, e.g., International Cosmetic Ingredient Dictionary and Handbook, 12$^{th}$ Edition, 2008 ("CTFA"), Volume 1, pages 458-60, which is incorporated by reference). In particular embodiments, the whole plant extract can be used (see pages 458-59 of the CTFA). A source that was used in the Examples was obtained from Bayer Sante Familiale SAS (France) under the trade name TECA (Titrated Extract of *Centella Asiatica*), which includes asiaticoside, madecassic acid, and asiatic acid.

As for *Vitis vinifera* seed extract, the *Vitis vinifera* plant is a vine that is native to the Mediterranean region, central Europe, and southwestern Asia. The extract is obtained from the seed of said plant. Further, *Vitis vinifera* seed extract is commercially available from a wide range of sources (see, e.g., CTFA, Volume 3, pages 2891-93, which is incorporated by reference). This extract can include polyphenols such as catechin and epicatechin and flaconoids.

Turning to *Magnolia* bark extract, the *Magnolia* plant is native to North America, China, Japan, and Russia. It is a large desiduous tree with brown bark. In particular aspects, the *Magnolia* bark is from *Magnolia grandiflora*, which is native to North America. In other aspects, it is from *Magnolia officinalis*, which is also native to China. In other instances, it can be from *Magnolia obovata*, which is native to Japan and Russia. The extract is obtained from the bark of the *Magnolia* plant, such as from *Magnolia grandiflora*, *Magnolia officinalis*, or *Magnolia obovata*. It can include compounds such as magnolol and honokiol. *Magnolia* bark extract is commercially available from a wide range of sources (see, e.g., CTFA, Volume 2, page 1500, which is incorporated by reference). A source that was used in the Examples was obtained from DSM (North America) and includes extract from the bark of *Magnolia grandiflora*, which includes magnolol and honokiol.

With respect to *Camellia sinensis* extract, the *Camellia sinensis* plant is native to China, and is a flowing plant. The extract can be obtained from the whole plant or parts of said plant. In particular instances, it is from the leaf, root, flower, or seed of said extract and in particular, the leaf. In particular instances the *Camellia sinensis* extract can include a polyphenol compound such as epigallocatechin gallate. *Camellia sinensis* extract, whether from the whole plant or parts of said plant, is commercially available from a wide range of sources (see, e.g., CTFA, Volume 1, pages 400-07, which is incorporated by reference). A source that was used in the Examples was obtained from DSM (North America) and includes epigallocatechin gallate (EGCG)—it is sold under the trade name Teavigo®.

Turning to Dihydroxymethylchromone (DHMC), it has the following chemical structure:

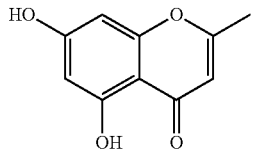

It is commercially available from EMD Chemicals (USA) under the trade name RonaCare® Luremin™. This is the source that was used in the Examples.

As for *Tambourissa trichophylla* leaf extract, *Tambourissa trichophylla* is a plant that is native to Madagascar. The extract is obtained from the leaf. *Tambourissa trichophylla* leaf extract is commercially available from a wide variety of sources (see, e.g., CTFA, Volume 3, page 2713, which is incorporated by reference).

In addition to the commercially availability of the extracts identified above, said extracts can be produced by obtaining the corresponding plant or portion thereof to produce the extract by extraction methods which are known to those of ordinary skill in the art. For instance, a person of ordinary skill in the art would be able to isolate any one of the extracts identified above from the whole plant or parts of the corresponding plant by using any suitable method known in the art. In one non-limiting example, the plant (or any part of the plant) can be disrupted by mechanical means which results in a puree. The puree is then processed to be substantially free of impurities or undesired solids. The puree can then be poured into a shallow vessel and quickly exposed to low temperature, i.e., flash frozen, for example at −20° C. or lower, preferably under a vacuum for removal of water content (lyophilization). The resultant extract can then be used in the compositions of the present invention.

In other aspects, aqueous, alcoholic, aqueous-alcoholic, or oil based extraction techniques, or combinations thereof, can be used on the whole plant or any part thereof of to produce an extract. In such a process, the desired part of the plant or the whole plant is crushed up (e.g., blender) and then subjected to a desired solvent (e.g., water, alcohol, water/alcohol, or oil based solvents) to obtain the desired extract. The extract can then be stored in liquid form, lyophilized, or subject to further processing techniques (e.g., heating, cooling, etc.). Extraction processes are well-known to those having ordinary skill in the extract field (e.g., maceration, infusion, percolation, digestion, decoction, hot continuous extraction, aqueous-alcoholic extract, counter current extract, microwave assisted extraction, ultrasound extraction, supercritical fluid extracts, phytonic extract (e.g., with hydro-flouro-carbon solvents), etc.

B. Compositions of the Present Invention

It is contemplated that the compositions of the present invention can include any of the skin actives or any combination thereof described throughout this specification. In particular aspects, the skin actives can be combined (e.g., *Centella asiatica*, *Vitis vinifera* seed, *Magnolia* bark, *Camellia sinensis*, and dihydroxymethylchromone). The compositions can include any number of combinations of additional ingredients described throughout this specification. The concentrations of the any ingredient within the compositions can vary. In non-limiting embodiments, for example, the compositions can comprise, consisting essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

The disclosed compositions of the present invention may also include various antioxidants to retard oxidation of one or more components. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

C. Vehicles

The compositions of the present invention can be incorporated into all types of vehicles. Non-limiting examples of suitable vehicles include emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydro-alcoholic), anhydrous bases (such as lipsticks and powders), gels, and ointments or by other method or any combination of the forgoing as would be known to one of ordinary skill in the art (Remington's, 1990). Variations and other appropriate vehicles will be apparent to the skilled artisan and are appropriate for use in the present invention. In certain aspects, it is important that the concentrations and combinations of the compounds, ingredients, and agents be selected in such a way that the combinations are chemically compatible and do not form complexes which precipitate from the finished product.

It is also contemplated that ingredients identified throughout this specification, including but not limited to *Centella asiatica, Vitis vinifera* seed, *Magnolia* bark, *Camellia sinensis*, or dihydroxymethylchromone, or any combinations thereof, can be individually or combinatorially encapsulated for delivery to a target area such as skin. Non-limiting examples of encapsulation techniques include the use of liposomes, vesicles, and/or nanoparticles (e.g., biodegradable and non-biodegradable colloidal particles comprising polymeric materials in which the ingredient is trapped, encapsulated, and/or absorbed—examples include nanospheres and nanocapsules) that can be used as delivery vehicles to deliver the ingredient to skin (see, e.g., U.S. Pat. Nos. 6,387,398; 6,203,802; 5,411,744; Kreuter 1998).

D. Cosmetic Products and Articles of Manufacture

The composition of the present invention can also be used in many cosmetic products including, but not limited to, sunscreen products, sunless skin tanning products, hair products, finger nail products, moisturizing creams, skin benefit creams and lotions, softeners, day lotions, gels, ointments, foundations, night creams, lipsticks, cleansers, toners, masks, or other known cosmetic products or applications. Additionally, the cosmetic products can be formulated as leave-on or rinse-off products. In certain aspects, the compositions of the present invention are stand-alone products.

E. Additional Ingredients

In addition to the *Centella asiatica, Vitis vinifera* seed, *Magnolia* bark, and *Camellia sinensis*, and dihydroxymethylchromone ingredients disclosed throughout this specification, compositions of the present invention can include additional ingredients such as cosmetic ingredients and pharmaceutical active ingredients. Non-limiting examples of these additional ingredients are described in the following subsections.

1. Cosmetic Ingredients

The CTFA International Cosmetic Ingredient Dictionary and Handbook (2004 and 2008) describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as paraaminobenzoic acid ("PABA") and corresponding PABA derivatives, titanium dioxide, zinc oxide, etc.), essential oils, vitamins (e.g. A, B, C, D, E, and K), trace metals (e.g. zinc, calcium and selenium), anti-irritants (e.g. steroids and non-steroidal anti-inflammatories), botanical extracts (e.g. aloe vera, chamomile, cucumber extract, *Ginkgo biloba*, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, and manitol), exfoliants, waterproofing agents (e.g., magnesium/aluminum hydroxide stearate), skin conditioning agents (e.g., aloe extracts, allantoin, bisabolol, ceramides, dimethicone, hyaluronic acid, and dipotassium glycyrrhizate). Non-limiting examples of some of these ingredients are provided in the following subsections.

a. UV Absorption Agents

UV absorption agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloy trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutyiphenol, and bis-ethylhexyloxyphenol methoxyphenyltriazine, 4-methylbenzylidenecamphor, and isopentyl 4-methoxycinnamate. Non-limiting examples of physical sunblocks include, kaolin, talc, petrolatum and metal oxides (e.g., titanium dioxide and zinc oxide).

b. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, alanine, algae extract, aloe barbadensis, aloe-barbadensis extract, aloe barbadensis gel, *Althea officinalis* extract, apricot (*Prunus armeniaca*) kernel oil, arginine, arginine aspartate, *Arnica montana* extract, aspartic acid, avocado (*Persea gratissima*) oil, barrier sphingolipids, butyl alcohol, beeswax, behenyl alcohol, beta-sitosterol, birch (*Betula alba*) bark extract, borage (*Borago officinalis*) extract, butcherbroom (*Ruscus aculeatus*) extract, butylene glycol, *Calendula officinalis* extract, *Calendula officinalis* oil, candelilla (*Euphorbia cerifera*) wax, canola oil, caprylic/capric triglyceride, cardamon (*Elettaria cardamomum*) oil, carnauba (*Copernicia cerifera*) wax, carrot (*Daucus carota sativa*) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, *Eucalyptus globulus* oil, evening primrose (*Oenothera biennis*) oil, fatty acids, geranium maculatum oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*Vitis vinifera*) seed oil, hazel (*Corylus americana*) nut oil, hazel (*Corylus avellana*) nut oil, hexylene glycol, hyaluronic acid, hybrid safflower (*Carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*Citrus medica limonum*) oil, linoleic acid, linolenic acid, macadamia ternifolia nut oil, maltitol, matricaria (*Chamomilla recutita*) oil, methyl glucose sesquistearate, methylsilanol PCA, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*Citrus aurantium dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, pentadecalactone, peppermint (*Mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*Oryza sativa*) bran oil, RNA, rosemary (*Rosmarinus officinalis*) oil, rose oil, safflower (*Carthamus tinctorius*) oil, sage (*Alvia officinalis*) oil, sandalwood (*Santalum album*) oil, serine, serum protein, sesame (*Sesamum indicum*) oil, shea butter (*Butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang ylang (*Cananga odorata*) oil.

c. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

d. Structuring Agents

In other non-limiting aspects, the compositions of the present invention can include a structuring agent. Structuring agent, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

e. Emulsifiers

In certain aspects of the present invention, the compositions do not include an emulsifier. In other aspects, however, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof.

f. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Michigan Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Michigan g. Essential Oils Essential oils include oils derived from herbs, flowers, trees, and other plants. Such oils are typically present as tiny droplets between the plant's cells, and can be extracted by several methods known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

h. Thickening Agents

Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene or trihydroxystearin, or a mixture of both.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379.

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboxymethyl dextran, sodium carrageenan, tragacanth gum, xanthan gum, and mixtures thereof.

i. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal or combinations thereof.

2. Pharmaceutical Ingredients

Pharmaceutical active agents are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

F. Kits

Kits are also contemplated as being used in certain aspects of the present invention. For instance, compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions.

EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

*Centella asiatica* extract and *Vitas vinifera* seed extract were both found to promote endothelial tube disruption. Dihydroxymethylchromone was found to thicken the epidermis. *Magnolia grandiflora* bark extract was found to inhibit angiogenesis. *Camellia sinensis* having epigallocatechin gallate was found to be a vasoconstricting agent on veins and small blood vessels such as arterioles, a capillaries, and venules. Data not shown.

An in vivo study was performed on 36 female panelists between the ages of 18-65 to evaluate the ability of the combination of the above-mentioned five ingredients to treat telangiectasias. Each panelists had mild to moderate telangiectasias. The study required 4 visits to the testing facility over a 12 week period. On the first visit (baseline), a lab technician marked the area of interest (approximately 5×5 cm$^2$) on the panelist's legs using a skin marker. During all the visits, panelists were visually graded by an expert grader for capillary color, capillary branching, visible erythema and dryness surrounding the spider veins and overall appearance of spider veins using a scale from 0 to 5 (0=none, 5=severe). The grading was followed by taking a set of photographs of the test site using Fuji S2 digital camera. The photographs were analyzed for capillary length and capillary number using Image Pro software. Panelists were instructed to apply a composition of the type described in Table 3 twice a day for 12 weeks to the designated test site on one leg (the additional ingredients (i.e., ingredients other than the five actives noted above) in the Table 3 formulation are not believed to contribute to the data in Tables 1 and 2 below). Panelists were refrained from applying any moisturizer on their legs 8 hours prior to their visit to the testing facility. Changes in visual grading scores and the image analysis data obtained at weeks 4, 8 and 12 were compared to baseline using paired t-test. Statistical significance was considered at p value ≤0.05. Table 1 provides date concerning expert grading, and Table 2 provides data concerning image analysis.

TABLE 1

(Expert Grading)

| Spider Vein Attributes | Mean Percent Improvement Compared to Baseline Over 12 Weeks [Percent of Panelists Showing Improvement] | | |
|---|---|---|---|
| | Week 4 | Week 8 | Week 12 |
| Capillary Color | 14%* | 10%* | 17%* |
| Capillary Branching | [44%] | [53%] | [56%] |
| Overall Appearance | [NS] | [NS] | [NS] |
| Visible Erythema Surrounding Spider Veins | [NS] [NS] | [NS] [NS] | [NS] [NS] |
| Visible Dryness Surrounding Spider Veins | 83%** [83%] | 94%** [100%] | 100%** [100%] |

*Statistically significant compared to baseline at a 95% confidence level.;
NS is not significant at 95% confidence level.
**Based on N = 6 at baseline.

TABLE 2

(Image Analysis)

| Spider Vein Attributes | Mean Percent Improvement Compared to Baseline Over 12 Weeks [Percent of Panelists Showing Improvement] | | |
|---|---|---|---|
| | Week 4 | Week 8 | Week 12 |
| Capillary Length (mm) | [NS] [NS] | 11%* [69%] | 12%* [72%] |
| Capillary Number | [NS] [NS] | 15%* [69%] | 13% [58%] |

*Statistically significant compared to baseline at a 95% confidence level.;
NS is not significant at 95% confidence level.

Table 3[1]

| Ingredient | % Concentration (by weight) |
|---|---|
| Phase A | |
| Water | 28.29 |
| SD-Alcohol 40B[2] | 60 |
| Pentylene Glycol | 5 |
| Ethoxydiglycol | 1.5 |
| Phase B | |
| *Magnolia grandiflora* bark extract[3] | 0.1 |
| *Centella asiatica* extract[4] | 0.1 |
| *Vitis vinifera* seed extract[5] | 0.5 |
| Caffeine | 1 |
| Argatensyl LS 9735[6] | 1 |
| Proteasyl TP POE LS 9818[7] | 1 |
| Epigallocatechin gallate from *Camellia sinensis* leaf extract[8] | 0.01 |
| Dihydroxy methylchromone[9] | 0.5 |
| Phase C | |
| Aristoflex AVC[10] | 1 |

[1]Can be prepared by adding all ingredients in phase A, following by adding phase B ingredients, followed by adding phase C ingredients. One can heat phase A to 70-75° C. and then add phase B with mixing following by adding phase C with continuous mixing and cool the mixture to room temperature (approximately 20-25° C.) and continue mixing until a uniform gel is obtained.
[2]Specially denatured (SD) alcohol is a mixture of ethanol with a denaturing agent (i.e., denatonium benzoate).
[3]Sold by DSM (North America). It is extract obtained from the bark of *Magnolia grandiflora*.
[4]Sold by Bayer Sante Familiale SAS (France) under the trade name TECA (Titrated Extract of *Centella Asiatica*). Extract is obtained from the leaves of *Centella asiatica*.
[5]Available from a wide range of sources (see CTFA).
[6]Sold by Laboratoires Serobiologiques (France). It is a mixture of water/*Argania spinosa* kernel extract/Sodium Cocoyl Glutamate/Carbomer.
[7]Sold by Cognis Corporation, which is a part of BASF (USA). It is a protein derived from the pea plant.
[8]Sold by DSM (North America) under the trade name Teavigo ®. Green tea extract that includes Epigallocatechin Gallate (EGCG).
[9]Sold by EMD Chemicals (USA) under the trade name of RonaCare ® Luremin ™.
[10]Sold by Clariant (USA). It is a synthetic polymer used as a gelling agent for aqueous systems and as a texturizer and thickener for oil-in-water emulsions.

The spider vein formulation significantly reduced the capillary color around the spider veins at weeks 4, 8 and 12 compared to baseline. The spider vein cream significantly reduced visible dryness around spider veins (N=6 at baseline) at weeks 4, 8 and 12 compared to baseline. The spider vein cream significantly reduced the capillary length and the capillary number of spider veins at weeks 8 and 12 compared to baseline.

In addition to the above tests, a person having ordinary skill in the art could also use the testing vehicle in Tables 4 and 5 to determine the effects of this combination of ingredients on telangiectasia.

TABLE 4*

| Ingredient | % Concentration (by weight) |
| --- | --- |
| Phase A | |
| Water | q.s. to 100 |
| Xanthum gum | 0.1 |
| M-paraben | 0.15 |
| P-paraben | 0.1 |
| Citric acid | 0.01 |
| Phase B | |
| Cetyl alcohol | 4.0 |
| Glyceryl stearate + PEG 100 | 4.0 |
| Octyl palmitate | 4.0 |
| Dimethicone | 1.0 |
| Tocopheryl acetate | 0.2 |
| Phase C | |
| Active Ingredients** | 2.0 |

*Sprinkle Xanthum gum in water and mix for 10 min. Subsequently, add all ingredients in phase A and heat to 70-75° C. Add all items in phase B to separate beaker and heat to 70-75° C. Mix phases A and B at 70-75° C. Continue mixing and allow composition to cool to 30° C. Subsequently, add phase C ingredient while mixing.
**Any of the active ingredients (or combination thereof) described in the specification can be used. For instance, the active ingredients can include *Centella asiatica* extract, *Vitis vinifera* seed extract, *Magnolia* bark extract, *Camellia sinensis* extract, and/or Dihydroxy methylchromone, or any combinations thereof. Although the total amount of active ingredients in the Table 1 formulation is 2% w/w, it is contemplated that the amount of active ingredients can be increased or decreased to achieve a desired result, where the water amount can be increased/decreased accordingly (e.g., q.s.).

TABLE 5*

| Ingredient | % Concentration (by weight) |
| --- | --- |
| Phase A | |
| Water | q.s. to 100 |
| M-paraben | 0.2 |
| P-paraben | 0.1 |
| Na2 EDTA | 0.1 |
| Shea butter | 4.5 |
| Petrolatum | 4.5 |
| Glycerin | 4.0 |
| Propylene Glycol | 2.0 |
| Finsolve TN | 2.0 |
| Phase B | |
| Sepigel 305 | 2.0 |
| Phase C | |
| Active Ingredient(s)** | 2.0 |

*Add ingredients in phase A to beaker and heat to 70-75° C. while mixing. Subsequently, add the phase B ingredient with phase A and cool to 30° C. with mixing. Subsequently, add phase C ingredient while mixing.
**Any of the active ingredients (or combination thereof) described in the specification can be used. For instance, the active ingredients can include *Centella asiatica* extract, *Vitis vinifera* seed extract, *Magnolia* bark extract, *Camellia sinensis* extract, and/or Dihydroxy methylchromone, or any combinations thereof. Although the total amount of active ingredients in the Table 1 formulation is 2% w/w, it is contemplated that the amount of active ingredients can be increased or decreased to achieve a desired result, where the water amount can be increased/decreased accordingly (e.g., q.s.).

Example 2

Additional Assays that can be Used to Test Compositions

The efficacy of the combination of ingredients disclosed throughout the specification and claims can be determined by using the following assays.

Oxygen Radical Absorbance Capacity (ORAC) Assay: An assay that measures the antioxidant activity of an ingredient or composition. In essence, it can quantify the degree and length of time it takes to inhibit the action of an oxidizing agent such as oxygen radicals that are known to cause damage cells (e.g., skin cells). The ORAC value of the compositions of the present invention can be determined by methods known to those of ordinary skill in the art (see U.S. Publication Nos. 2004/0109905 and 2005/0163880; Cao et al. (1993)), all of which are incorporated by reference). In summary, the assay described in Cao et al. (1993) measures the ability of antioxidant compounds in test materials to inhibit the decline of B-phycoerythrm (B-PE) fluorescence that is induced by a peroxyl radical generator, AAPH.

Erythema Assay: An assay to measure the reduction of skin redness can be evaluated using a Minolta Chromometer. Skin erythema may be induced by applying a 0.2% solution of sodium dodecyl sulfate on the forearm of a subject. The area is protected by an occlusive patch for 24 hrs. After 24 hrs, the patch is removed and the irritation-induced redness can be assessed using the a* values of the Minolta Chroma Meter. The a* value measures changes in skin color in the red region. Immediately after reading, the area is treated with a composition of the present invention. Repeat measurements are taken at regular intervals to determine the formula's ability to reduce redness and irritation.

Skin Moisture/Hydration Assay: Skin moisture/hydration benefits can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72° C.). Three separate impedance readings can be taken on each side of the face, recorded, and averaged. The T5 setting can be used on the impedance meter which averages the impedance values of every five seconds application to the face. Changes can be reported with statistical variance and significance.

Skin Clarity and Reduction in Freckles and Age Spots Assay: Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether a composition is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$.

Skin Dryness, Surface Fine Lines, Skin Smoothness, and Skin Tone Assay: Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical Grading of Skin Tone Assay: Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical Grading of Skin Smoothness Assay: Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin Smoothness and Wrinkle Reduction Assay With Methods Disclosed in Packman et al. (1978): Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin Firmness Assay with a Hargens Ballistometer: Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin Softness/Suppleness Assay with a Gas Bearing Electrodynamometer: Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

Appearance of Lines and Wrinkles Assay with Replicas: The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program.

Surface Contour of the Skin Assay with a Profilometer/Stylus Method: The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height (x-axis).

MELANODERM™ Assay: In other non-limiting aspects, the efficacy of the compositions of the present invention can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing the compositions and whitening agents of the present invention or with the base alone as a control. Alternatively, an untreated sample of the skin analog can be used as a control.

ORAC Assay: Oxygen Radical Absorption (or Absorbance) Capacity (ORAC) of the aromatic skin-active ingredients and compositions can also be assayed by measuring the antioxidant activity of such ingredients or compositions. This assay can quantify the degree and length of time it takes to inhibit the action of an oxidizing agent such as oxygen radicals that are known to cause damage cells (e.g., skin cells). The ORAC value of the aromatic skin-active ingredients and compositions can be determined by methods known to those of ordinary skill in the art (see U.S. Publication Nos. 2004/0109905 and 2005/0163880; Cao et al. (1993)), all of which are incorporated by reference). In summary, the assay described in Cao et al. (1993) measures the ability of antioxidant compounds in test materials to inhibit the decline of B-phycoerythrm (B-PE) fluorescence that is induced by a peroxyl radical generator, AAPH.

Matrix Metalloproteinase Enzyme Activity (MMP3; MMP9) Assay: An in vitro matrix metalloprotease (MMP) inhibition assay. MMPs are extracellular proteases that play a role in many normal and disease states by virtue of their broad substrate specificity. MMP3 substrates include collagens, fibronectins, and laminin; while MMP9 substrates include collagen VII, fibronectins and laminin. Using Colorimetric Drug Discovery kits from BioMol International for MMP3 (AK-400) and MMP-9 (AK-410), this assay is designed to measure protease activity of MMPs using a thiopeptide as a chromogenic substrate (Ac-PLG-[2-mercapto-4-methyl-pentanoyl]-LG-OC2H5)5,6. The MMP cleavage site peptide bond is replaced by a thioester bond in the thiopeptide. Hydrolysis of this bond by an MMP produces a sulfhydryl group, which reacts with DTNB [5,5'-dithiobis(2-nitrobenzoic acid), Ellman's reagent] to form 2-nitro-5-thiobenzoic acid, which can be detected by its absorbance at 412 nm ($\varepsilon$=13,600 M-1cm-1 at pH 6.0 and above 7).

All of the skin-active ingredients, compositions, or methods disclosed and claimed in this specification can be made and executed without undue experimentation in light of the present disclosure. While the skin-active ingredients, compositions, or methods of this invention have been described in terms of particular embodiments, it will be apparent to those of skill in the art that variations may be applied to the skin-active ingredients, compositions, or methods and in the steps or in the sequence of steps of the method described herein without departing from the concept, spirit and scope of the invention.

The invention claimed is:

1. A method of treating telangiectasia by disrupting endothelial tubes in skin of a subject in need thereof; the method comprising administering to said skin of the subject a composition comprising: water, citric acid, cetyl alcohol, glyceryl stearate, a vitamin E, *Butyrospermum parkii* butter, carbomer, sodium cocoyl glutamate, glycerin, an effective amount of a combination of an extract of *Centella asiatica* leaf, an extract of *Camellia sinensis* leaf, and an extract of *Vitis vinifera* seed, wherein the effective amount treats telangiectasia and disrupts endothelial tubes in the skin, and one or more of *Cocos nucifera* oil, Aloe barbadensis extract, stearic acid, phenoxyethanol, jojoba oil, *Daucus carota sativa* oil, *Triticum vulgare* germ oil, *Lavandula angustifolia* oil, *Rosmarinus officinalis* oil, lemongrass oil, *Macadamia ternifolia* nut oil, a vitamin C, cypress oil, and tea tree oil.

2. The method of claim 1, wherein the composition is applied to spider veins present on the subject's skin.

3. The method of claim 2, wherein the spider veins are present on facial skin, leg skin, ankle skin, or arm skin.

4. The method of claim 3, wherein the spider veins are present on leg skin and the composition is applied to the spider veins on the leg skin.

5. The method of claim 2, wherein the composition remains on the skin for at least 5 minutes after topical application.

6. The method of claim 2, wherein the composition is a cream, gel, or lotion.

7. The method of claim 2, wherein the composition is an emulsion.

8. The method of claim 2, wherein the composition further comprises a moisturization agent, a UV absorbing agent, anti-oxidant, structuring agent, emulsifier, silicone containing compound, essential oil, thickening agent, and a preservative.

9. The method of claim 1, wherein the composition comprises:
   –0.01 to 1% by weight of the extract of *Centella asiatica* leaf and
   –0.01 to 1% by weight of the extract of *Vitis vinifera* seed.

10. The method of claim 1, wherein the *Centella asiatica* leaf extract comprises asiaticoside, madecassic acid, and asiatic acid, wherein the extract of *Camellia sinensis* leaf comprises epigallocatechin gallate, and wherein the *Vitis vinifera* seed extract comprises polyphenols.

11. The method of claim 1, wherein the *Centella asiatica* leaf extract is an aqueous, alcoholic, or hydro-alcoholic extract, wherein the extract of *Camellia sinensis* leaf is an aqueous, alcoholic, or hydro-alcoholic extract, and wherein the *Vitis vinifera* seed extract is an aqueous, alcoholic, or hydro-alcoholic extract.

12. The method of claim 1, wherein the composition comprises: *Cocos nucifera* oil; Aloe barbadensis extract; stearic acid; phenoxyethanol; jojoba oil; *Daucus carota sativa* oil; *Triticum vulgare* germ oil; *Lavandula angustifolia* oil; *Rosmarinus officinalis* oil; lemongrass oil; *Macadamia ternifolia* nut oil; a vitamin C; cypress oil; and tea tree oil.

* * * * *